United States Patent
Frumkin et al.

(10) Patent No.: US 12,378,602 B2
(45) Date of Patent: *Aug. 5, 2025

(54) METHODS AND KITS FOR DETERMINING THE EFFICIENCY OF PLASMA SEPARATION FROM WHOLE BLOOD

(71) Applicant: NUCLEIX LTD., Rehovot (IL)

(72) Inventors: Danny Frumkin, Rehovot (IL); Adam Wasserstrom, Ness Ziona (IL); Revital Knirsh, Rosh HaAyin (IL)

(73) Assignee: NUCLEIX LTD., Rehovot (IL)

( * ) Notice: Subject to any disclaimer, the term of this patent is extended or adjusted under 35 U.S.C. 154(b) by 214 days.

This patent is subject to a terminal disclaimer.

(21) Appl. No.: 18/135,424

(22) Filed: Apr. 17, 2023

(65) Prior Publication Data

US 2024/0002923 A1 Jan. 4, 2024

Related U.S. Application Data

(63) Continuation of application No. 16/970,700, filed as application No. PCT/IL2019/050201 on Feb. 20, 2019, now Pat. No. 11,629,375.

(60) Provisional application No. 62/633,094, filed on Feb. 21, 2018.

(51) Int. Cl.
C12Q 1/68 (2018.01)
C12Q 1/6851 (2018.01)
C12Q 1/686 (2018.01)

(52) U.S. Cl.
CPC ........... *C12Q 1/686* (2013.01); *C12Q 1/6851* (2013.01)

(58) Field of Classification Search
None
See application file for complete search history.

(56) References Cited

U.S. PATENT DOCUMENTS

| | | | |
|---|---|---|---|
| 2009/0280479 A1* | 11/2009 | Hoon | C12Q 1/6806 435/6.12 |
| 2010/0041048 A1* | 2/2010 | Diehl | C12Q 1/6886 435/6.16 |
| 2013/0224740 A1* | 8/2013 | Thierry | C12Q 1/686 435/6.12 |
| 2016/0018360 A1 | 1/2016 | Yang | |

(Continued)

FOREIGN PATENT DOCUMENTS

| | | |
|---|---|---|
| CA | 2906818 A1 | 9/2014 |
| CN | 104313011 A | 1/2015 |

(Continued)

OTHER PUBLICATIONS

Fleischhacker et al, Circulating nucleic acids (CNAs) and cancer—a survey, Biochim Biophys Acta. Jan. 2007;1775(1):181-232. doi: 10.1016/j.bbcan.2006.10.001. Epub Oct. 7, 2006.*

(Continued)

*Primary Examiner* — Aaron A Priest
(74) *Attorney, Agent, or Firm* — Michael A. Whittaker

(57) ABSTRACT

Methods and kits for determining the efficiency of plasma separation from whole blood are provided, using real-time PCR amplification of two amplicons, namely, a short amplicon of e.g. 70-150 bps and a long amplicon of e.g. 350-600 bps. The separation efficiency is determined based on the difference in amplification patterns of the two amplicons.

14 Claims, 1 Drawing Sheet

Specification includes a Sequence Listing.

(56) References Cited

U.S. PATENT DOCUMENTS

| | | | |
|---|---|---|---|
| 2016/0186239 A1* | 6/2016 | Sinha | C12Q 1/6851 |
| | | | 506/9 |
| 2018/0105864 A1* | 4/2018 | Murtaza | C12Q 1/6876 |
| 2019/0225958 A1* | 7/2019 | Steffen | C12Q 1/6834 |

FOREIGN PATENT DOCUMENTS

| | | | | |
|---|---|---|---|---|
| EP | 3358020 A2 | 8/2018 | | |
| WO | WO-2012028746 A1 * | 3/2012 | | C12Q 1/6851 |
| WO | 2018031929 A1 | 2/2018 | | |

OTHER PUBLICATIONS

Devonshire et al, Towards standardisation of cell-free DNA measurement in plasma: controls for extraction efficiency, fragment size bias and quantification, Anal Bioanal Chem. Oct. 2014;406(26):6499-512. doi: 10.1007/s00216-014-7835-3. Epub May 24, 2014.*

Wang et al, Increased plasma DNA integrity in cancer patients, Cancer Res. Jul. 15, 2003;63(14):3966-8; Boynton et al., DNA integrity as a potential marker for stool-based detection of colorectal cancer, Clin Chem. Jul. 2003;49(7):1058-65. doi: 10.1373/49.7.1058.*

Boynton et al., DNA Integrity as a Potential Marker for Stool-based Detection of Colorectal Cancer. Clin Chem. Jul. 2003;49(7):1058-1065.

Chan et al., Size Distributions of Maternal and Fetal DNA in Maternal Plasma. Clin Chem. Jan. 2004;50(1):88-92.

Devonshire et al., Towards standardisation of cell-free DNA measurement in plasma: controls for extraction efficiency, fragment size bias and quantification. Anal Bioanal Chem. Oct. 2014;406(26):6499-6512.

Fernando et al., A new methodology to preserve the original proportion and integrity of cell-free fetal DNA in maternal plasma during sample processing and storage. Prenat Diagn. May 2010;30(5):418-424.

Fleischhacker and Schmidt, Circulating nucleic acids (CNAs) and cancer—A survey. Biochim Biophys Acta. Jan. 2007;1775(1):181-232.

Grolz et al., Liquid Biopsy Preservation Solutions for Standardized Pre-Analytical Workflows-Venous Whole Blood and Plasma. Curr Pathobiol Rep. 2018;6(4):275-286.

Malentacchi et al., Influence of storage conditions and extraction methods on the quantity and quality of circulating cell-free DNA (ccfDNA): the SPIDIA-DNAplas External Quality Assessment experience. Clin Chem Lab Med. Nov. 2015;53(12):1935-1942.

Medina Diaz et al., Performance of Streck cfDNA Blood Collection Tubes for Liquid Biopsy Testing. PLoS One. Nov. 10, 2016;11(11):e0166354; 18 pages.

Nikolaev et al., Circulating tumoral DNA: Preanalytical validation and quality control in a diagnostic laboratory. Anal Biochem. Feb. 1, 2018;542:34-39.

Norton et al., A stabilizing reagent prevents cell-free DNA contamination by cellular DNA in plasma during blood sample storage and shipping as determined by digital PCR. Clin Biochem. Oct. 2013;46(15):1561-1565.

Wang et al., Increased Plasma DNA Integrity in Cancer Patients. Cancer Res. Jul. 15, 2003;63(14):3966-3968.

Ward Gahlawat et al., (2019) Evaluation of Storage Tubes for Combined Analysis of Circulating Nucleic Acids in Liquid Biopsies. Int J Mol Sci. Feb. 6, 2019;20(3):704; 10 pages.

Grabuschnig et al., Circulating cell-free DNA is predominantly composed of retrotransposable elements and non-telomeric satellite DNA. J Biotechnol. Apr. 10, 2020:313:48-56.

Ivanov et al., Non-random fragmentation patterns in circulating cell-free DNA reflect epigenetic regulation. BMC Genomics. 2015;16 Suppl 13(Suppl 13):S1.

Ivanov et al., Utility of cfDNA Fragmentation Patterns in Designing the Liquid Biopsy Profiling Panels to Improve Their Sensitivity. Front Genet. Mar. 12, 2019:10:194.

Ma et al., Cell-Free DNA Provides a Good Representation of the Tumor Genome Despite Its BiasedGRAB Fragmentation Patterns. PLoS One. Jan. 3, 2017;12(1):e0169231.

Ehrich et al., A new method for accurate assessment of DNA quality after bisulfite treatment. Nucleic Acids Res. 2007;35(5):e29. With Corrigendum (9 pages total).

Kersaudy-Kerhoas et al., Validation of a blood plasma separation system by biomarker detection. Lab Chip. Jun. 21, 2010;10(12):1587-1595.

Liu et al., A high-efficiency superhydrophobic plasma separator. Author manuscript; available in PMC Jan. 27, 2016. Published in final edited form as: Lab Chip. Feb. 7, 2016;16(3):553-560.

Syeda et al., Abstract 2239: Analysis of nucleosomal DNA as an extraction control for plasma-based circulating tumor DNA assays. Cancer Res. Jul. 1, 2019;79(13_Supplement):2239.

Jiang and Lo, The Long and Short of Circulating Cell-Free DNA and the Ins and Outs of Molecular Diagnostics. Trends Genet. Jun. 2016;32(6):360-371.

Pang et al., Size distribution of cell-free DNA in maternal plasma. International Journal of Laboratory Medicine 2009;30(11):1046-1048 Abstract only (incl Engl lang transl).

* cited by examiner

SEQUENCE LISTING

```
Sequence total quantity: 10
SEQ ID NO: 1             moltype = DNA  length = 126
FEATURE                  Location/Qualifiers
source                   1..126
                         mol_type = genomic DNA
                         organism = Homo sapiens
SEQUENCE: 1
gtctttgtga cattgagtta cagggctttg actcctgggt ctaaaaatta caccaaatat   60
tgttaaatct taaacactaa cagcaattca agcctcatct tcaggtcctg gagaagatgc  120
caatat                                                             126

SEQ ID NO: 2             moltype = DNA  length = 450
FEATURE                  Location/Qualifiers
source                   1..450
                         mol_type = genomic DNA
                         organism = Homo sapiens
SEQUENCE: 2
gtcagccttt attatcactt tgcaatacaa agaaagcaag gtgaagacta acttttctct   60
tgtacagaat catcaggcta aattttggc attatttcag tccttggaga catctgagag  120
attccgggat gccagtggtg cctctctggc cacactgaca acaaataatt cacctaagga  180
atagttcact tcagctattt tttgctactc attggttgtc agtgccattg aggagagctc  240
agtgtagatc aaagaaaacg gtgtagatca aagaaaacgg tgattcggtg attgttcccc  300
ttcttcccag ccacccacca tctgaaccta atgcatcatt gtacaatggc cgtaaaggat  360
gacaagggac tcagcaatca gttcctggag gaaatgatgc tgtggctttt ggctggtggc  420
accatcatcc tcagtcatca gtcagagtca                                   450

SEQ ID NO: 3             moltype = DNA  length = 23
FEATURE                  Location/Qualifiers
misc_feature             1..23
                         note = Primer
source                   1..23
```

```
                        mol_type = other DNA
                        organism = synthetic construct
SEQUENCE: 3
gtctttgtga cattgagtta cag                                              23

SEQ ID NO: 4           moltype = DNA   length = 22
FEATURE                Location/Qualifiers
misc_feature           1..22
                       note = Primer
source                 1..22
                       mol_type = other DNA
                       organism = synthetic construct
SEQUENCE: 4
atattggcat cttctccagg ac                                               22

SEQ ID NO: 5           moltype = DNA   length = 23
FEATURE                Location/Qualifiers
misc_feature           1..23
                       note = Primer
source                 1..23
                       mol_type = other DNA
                       organism = synthetic construct
SEQUENCE: 5
gtcagccttt attatcactt tgc                                              23

SEQ ID NO: 6           moltype = DNA   length = 22
FEATURE                Location/Qualifiers
misc_feature           1..22
                       note = Primer
source                 1..22
                       mol_type = other DNA
                       organism = synthetic construct
SEQUENCE: 6
tgactctgac tgatgactga gg                                               22

SEQ ID NO: 7           moltype = DNA   length = 520
FEATURE                Location/Qualifiers
source                 1..520
                       mol_type = genomic DNA
                       organism = Homo sapiens
SEQUENCE: 7
gatgcaatag tcagactggg aaaaggtaga tgaatggaaa aggcaaacag gtctttatga      60
aaaacaatgc agatgatctc tggtgtcaca taatgtttat tattattcag ctatgtacat     120
acttgaaaag atccattgtc attaaattat tttttatgtc agcctttatt atcactttgc     180
aatacaaaga aagcaaggtg aagactaact tttctcttgt acagaatcat caggctaaat     240
ttttggcatt atttcagtcc ttggagacat ctgagagatt ccgggatgcc agtggtgcct     300
ctctggccac actgacaaca aataattcac ctaaggaata gttcacttca gctattttt     360
gctactcatt ggttgtcagt gccattgagg agagctcagt gtagatcaaa gaaaacggtg     420
tagatcaaag aaaacggtga ttcggtgatt gttccccttc ttcccagcca cccaccatct     480
gaacctaatg catcattgta caatggccgt aaaggatgac                           520

SEQ ID NO: 8           moltype = DNA   length = 642
FEATURE                Location/Qualifiers
source                 1..642
                       mol_type = genomic DNA
                       organism = Homo sapiens
SEQUENCE: 8
atgaatggaa aaggcaaaca ggtctttatg aaaaacaatg cagatgatct ctggtgtcac      60
ataatgttta ttattattca gctatgtaca tacttgaaaa gatccattgt cattaaatta     120
tttttatgt cagcctttat tatcactttg caatacaaag aaagcaaggt gaagactaac     180
ttttctcttg tacagaatca tcaggctaaa ttttttggcat tatttcagtc cttggagaca     240
tctgagagat tccgggatgc cagtggtgcc tctctggcca cactgacaac aaataattca     300
cctaaggaat agttcacttc agctattttt tgctactcat tggttgtcag tgccattgag     360
gagagctcag tgtagatcaa agaaaacggt gtagatcaaa gaaaacggtg attcggtgat     420
tgttccccctt cttcccagcc acccaccatc tgaacctaat gcatcattgt acaatggccg     480
taaaggatga caagggactc agcaatcagt tcctggagga aatgatgctg tggcttttgg     540
ctggtggcac catcatcctc agtcatcagt cagagtcatc aaagtgatca ttcatccatt     600
cactccctcc tctgtctcca ccccacagct aatcaactaa cc                        642

SEQ ID NO: 9           moltype = DNA   length = 538
FEATURE                Location/Qualifiers
source                 1..538
                       mol_type = genomic DNA
                       organism = Homo sapiens
SEQUENCE: 9
tgaggtagag aaaagaatac tcatgttaaa gatagacatg gaagatataa aaaagaccaa      60
aatcaaactt ctagagatga aaatgtata ggatgggatc aatagcaaat tagtgcaaaa     120
aaagcaaact tgaaggcaca gcaaagaaa ccatccaaaa ttaaaacaaa gaaaggttg     180
gaaaaacata taaagcatca atgagttgag gaacaacttc aagcagtcta atatacatgt     240
```

```
aaatttgagt cccagaagga agaagtaaga gtagactata gaaaatttat tttaaggaat    300
agcaaaaatt tttccaaact gtatgtgaaa atagaaaact acatataaaa aatatgatta    360
caaacccaca gatccagtaa gttcaacaaa ccccaagcac agaacacatg aagaaagcta    420
aaccaatgta ccctataatt gaattgcaca aattcaatgg taaaaagaaa aatcttaaaa    480
gtagccagag tttttaaaaa aaaaaagaaa gaaaaaagac acttaacata cagaggag     538

SEQ ID NO: 10          moltype = DNA  length = 77
FEATURE                Location/Qualifiers
source                 1..77
                       mol_type = genomic DNA
                       organism = Homo sapiens
SEQUENCE: 10
agcaaggtga agactaactt ttctcttgta cagaatcatc aggctaaatt tttggcatta    60
tttcagtcct tggagac                                                  77
```

METHODS AND KITS FOR DETERMINING THE EFFICIENCY OF PLASMA SEPARATION FROM WHOLE BLOOD

FIELD OF THE INVENTION

The present invention relates to a real-time PCR assay for evaluating whether a plasma sample is sufficiently separated from the cellular fraction of whole blood. The present invention is advantageous for diagnostic tests that require utilizing circulating cell-free DNA.

SEQUENCE LISTING

The instant application contains a Sequence Listing which has been submitted electronically in .XML format and is hereby incorporated by reference in its entirety. Said .XML copy, created on Aug. 11, 2023, is named NUC-0002-CT1 and is 14 kilobytes in size. The sequence listing contained in this .XML file is part of the specification and is hereby incorporated by reference herein in its entirety.

BACKGROUND OF THE INVENTION

Circulating cell-free DNA (cfDNA) is DNA released by both normal and tumor cells into the blood circulation. The origin of cfDNA in blood is not fully understood but believed to be related to apoptosis, necrosis and active release from cells. The presence of cfDNA in blood was known for decades, however its true diagnostic potential has been realized only in recent years, resulting in an increasing interest in the detection and analysis of cfDNA. For example, fetal cfDNA present in maternal blood is now used for non-invasive prenatal diagnosis, and clinical studies are underway using tumor-derived CfDNA as surrogate markers in cancer patients.

Analysis of cfDNA first requires the separation of plasma (containing the cfDNA) from whole blood. Traditionally plasma is separated from blood by centrifugation or filtration. Newer microfluidic methods are currently emerging. Following separation, the cfDNA may be further purified by extraction before further analysis.

Effective cfDNA separation from the cellular fraction of the blood is highly important to the quality of cfDNA analysis, Contamination of the plasma with DNA released from white blood cells between the time of blood draw and processing of the plasma decreases the proportion of cfDNA in the sample and increases noise and inaccuracies to the cfDNA analysis. To evaluate separation efficiency, typically blood cell counts are performed, either manually using a hemocytometer or automatically using a flow cytometer. However, such methods have a number of drawbacks, where some are laborious and expensive and others are insufficiently accurate.

Studies have shown that circulating cfDNA is mostly fragments of less than 300 bps in length, and even less than 200 bps in length (Chan et al., 2004, Clinical Chemistry. 50(1): 88-92), while DNA originating from white blood cells is mostly long fragments of more than 10 Kbs.

Gel electrophoresis in which DNA is separated based on molecular size has been suggested for determining separation efficiency, by detecting the presence of long versus short DNA fragments. However, such method requires large amounts of DNA, which is a major difficulty when working with circulating cell-free DNA.

Norton ea al. (2013, Clinicol Biochemistry, 46: 1561-1565) studied the ability of a stabilizing agent to prevent contamination of cell-free DNA (cfDNA) by cellular genomic DNA (gDNA) during storage and shipping of blood samples. The contamination by gDNA was evaluated using digital PCR. In particular, digital PCR technology was utilized to quantify contaminating gDNA by amplifying a 420 bp DNA fragment from the r-actin gene. A secondi digital PCR assay was utilized to quantify cfDNA by amplifying a 136 bp shorter β-actin amplicon. Using these assays, the quality of a plasma cfDNA sample was determined, to evaluate the degree of gDNA contamination.

There is a need for improved methods and kits for determining the efficiency of plasma separation from whole blood, which are simple to operate, cost-effective and accurate.

SUMMARY OF THE INVENTION

The present invention provides according to some aspects methods and kits for determining the efficiency of plasma separation from whole blood using quantitative PCR amplification of two amplicons, namely, a short amplicon of e.g. 70-150 bps and a long amplicon of e.g. 350-600 bps. The separation efficiency is determined based on the difference in amplification levels of the two amplicons. Advantageously, the separation efficiency is determined without absolute quantification of DNA and/or determination of copy number of any gene/locus.

DNA in the plasma fraction of the blood is mostly short fragments of cell-free DNA, of up to about 300 bps in length. When the plasma fraction is not well separated from the cellular components of the blood, the plasma further contains DNA originating from white blood cells. The latter is mostly long fragments of more than 10 Kbs. Thus, the presence of long fragments of DNA in a plasma sample provides an indication regarding the efficiency of the plasma separation from whole blood.

In the methods disclosed herein, the short and long amplicons from a tested plasma sample are co-amplified and the amplification patterns are analyzed. According to the methods disclosed herein, in plasma samples that are well separated from the cellular fraction of the blood, a significant difference in the amplification levels of the two amplicons is observed, where the short amplicon is amplified with higher efficiency compared to the long amplicon. Without being bound to any theory or mechanism of action, the difference in the amplification levels reflects the proportion of short cell-free DNA relative to long DNA from white blood cells in the tested plasma sample, and is therefore indicative of the efficiency of plasma separation.

Advantageously, the difference in amplification levels is calculated between amplicons co-amplified from the same DNA template in the same reaction mixture (i.e., under the same reaction conditions). This set up renders the methods disclosed herein insensitive to various "noise" factors, such as changes in template DNA concentration, PCR conditions and presence of impurities/inhibitors. It should be noted that at no point the methods of the invention require absolute quantification of DNA and/or determination of copy number of any gene/locus. Thus, no actual amount, concentration and/or copy number of any genomic locus are associated with the methods of the invention. The methods disclosed herein therefore eliminate the need for standard curves and/or additional laborious steps involved in absolute quantification, thereby offering a simple and cost effective procedure without compromising on sensitivity, quality and/or accuracy. In addition, by employing real-time PCR, the methods are effective for any concentration of template DNA and do not require dilutions or other adjustments of the template.

According to one aspect, the present invention provides a method for determining the efficiency of plasma separation from whole blood, the method comprising:
(a) obtaining DNA from a plasma sample;
(b) generating by PCR co-amplification:
  (i) a first amplification product of 70-150 bps from a first genomic locus using a first primer pair, and
  (ii) a second amplification product of at least 350 bps from a second genomic locus using a second primer pair;
(c) calculating a signal intensity for each of said first and second amplification products; and
(d) determining that the plasma sample is separated when the difference between the signal intensities is above a predefined threshold,
wherein the first and second amplification products produce distinct signal intensity differences for plasma DNA and whole blood DNA.

In some embodiments, step (b) is performed using real-time PCR. In some embodiments, when step (b) is performed using real-time PCR, the method further comprises adding fluorescent probes for specifically detecting the first and second amplification products.

In some embodiments, when step (b) is performed using real-time PCR, the signal intensity is quantification cycle (Cq), and the plasma sample is determined to be separated based on the difference between the Cq values (ΔCq) of the first and second amplification products. In some embodiments, the plasma sample is determined to be separated when the ΔCq (Cq(second)−Cq(first)) is above a predefined threshold ΔCq.

In sortie embodiments, the first and second primer pairs are of equal efficiency.

In some embodiments, the first amplification product is of 100-150 bps.

In some embodiments, the second amplification product is of 350-700 bps. In some embodiments, the second amplification product is of 350-650 bps. In some embodiments, the second amplification product is of 350-550 bps.

In some embodiments, the first amplification product comprises a sequence selected from the group consisting of SEQ ID NO: 1 and SEQ ID NO: 10. Each possibility represents a separate embodiment of the present invention. In some embodiments, the first amplification product consists of the sequence set forth in SEQ ID NO: 1 or SEQ ID NO: 10. Each possibility represents a separate embodiment of the present invention.

In some embodiments, the second amplification product comprises a sequence selected from the group consisting of SEQ ID NO: 2, SEQ ID NO: 7, SEQ ID NO: 8 and SEQ ID NO: 9. Each possibility represents a separate embodiment of the present invention. In some embodiments, the second amplification product consists of the sequence set forth in SEQ ID NO: 2, SEQ ID NO: 7, SEQ ID NO: 8 or 0.30 SEQ ID NO: 9. Each possibility represents a separate embodiment of the present invention.

In some embodiments, the first and second amplification products comprise sequences as set forth in SEQ ID NO: 1 and SEO ID NO: 2, respectively. In some particular embodiments, the first and second amplification products consist of sequences as set forth in SEQ ID NO: 1 and SEQ ID NO: 2, respectively.

In some embodiments, the plasma sample is derived from a human blood sample.

According to a further aspect, the present invention provides a kit for determining the efficiency of plasma separation from whole blood, comprising:
(i) a first primer pair, for generating by PCR a first amplification product of 70-150 bps from a first genomic locus;
(ii) a second primer pair, for generating by PCR a second amplification product of at least 350 bps, from a second genomic locus; and
(iii) probes for detecting the first and second amplification products, to determine a signal intensity for each amplification product,
wherein the first and second amplification products produce distinct signal intensity differences for plasma DNA and whole blood DNA.

In some embodiments, the kit further comprises an instruction manual directing the correlation between signal intensity differences and level of separation. In some embodiments, the instruction manual provides a threshold signal intensity difference between the first and second amplification products, above which a plasma sample is determined to be separated. In some particular embodiments, the instruction manual provides a threshold ΔCq (Cq(second)−Cq(first)), above which a plasma sample is determined to be separated.

In some embodiments, the probes are fluorescently-labeled oligonucleotide probes.

In some embodiments, the first and second primer pairs are of equal efficiency.

In some embodiments, the first amplification product is of 100-150 bps.

In some embodiments, the second amplification product is of 350-700 bps. In some embodiments, the second amplification product is of 350-650 bps. In some embodiments, the second amplification product is of 350-550 bps.

In some embodiments, the first amplification product comprises a sequence selected from the group consisting of SEQ ID NO: 1 and SEQ ID NO: 10. In some embodiments, the first amplification product consists of the sequence set forth in SEQ ID NO: 1 or SEQ ID NO: 10.

In some embodiments, the second amplification product comprises a sequence selected from the group consisting of SEQ ID NO: 2, SEQ ID NO: 7, SEQ ID NO: 8 and SEQ ID NO: 9. In some embodiments, the second amplification product consists of the sequence set forth in SEQ ID NO: 2, SEQ ID NO: 7, SEQ ID NO: 8 or SEQ ID NO: 9.

In some embodiments, the first and second amplification products comprise sequences as set forth in SEQ ID NO: 1 and SEQ ID NO: 2, respectively. In some particular embodiments, the first and second amplification products consist of sequences as set forth in SEQ ID NO: 1 and SEQ ID NO: 2, respectively.

In some embodiments, the first primer pair is SEQ ID NO: 3 (forward) and SEQ ID NO: 4 (reverse).

In some embodiments, the second primer pair is SEQ ID NO: 5 (forward) and SEQ ID NO: 6 (reverse).

In some embodiments, the first primer pair is SEQ ID NO: 3 (forward) and SEQ ID NO: 4 (reverse), and the second primer pair is SEQ ID NO: 5 (forward) and SEQ ID NO: 6 (reverse).

These and further aspects and features of the present invention will become apparent from the detailed description, examples and claims which follow.

DETAILED DESCRIPTION OF THE INVENTION

Figure 1A:
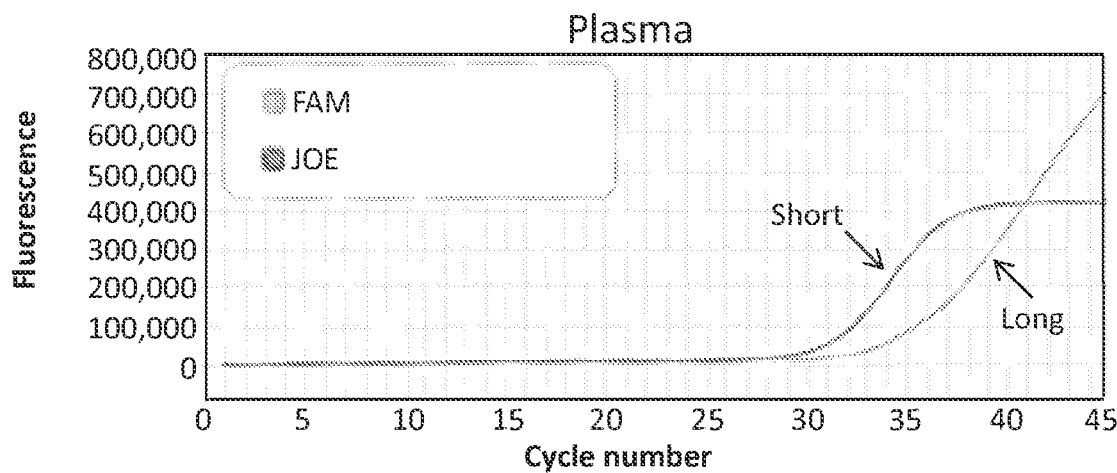
FIGS. 1A-C show exemplary quantitative PCR plots of short ("JOE") and long ("FAM") amplification products in DNA samples from plasma (A), plasma contaminated with leukocytes (B) and DNA from whole blood (C).

The present invention relates to determining the efficiency of plasma separation from the cellular fraction of whole blood using real-time PCR amplification of two amplicons, namely, a short amplicon of 70-150 bps and a long amplicon of at least 350 bps.

DNA found in plasma ("plasma DNA") is mostly cell-free DNA, which typically includes DNA fragments having less than 300 bp in length. In contrast, DNA in whole blood ("whole blood DNA") is mostly DNA released from white blood cells, which typically includes DNA fragments of more than 10 Kb. The difference in DNA contents between plasma and whole blood in terms of the proportion of short versus long DNA fragments establishes different amplification patterns of the short and long amplicons, which enables determining the separation efficiency of a plasma sample from the cellular components of the blood.

As used herein, the terms "cell-free DNA" and "circulating cell-free DNA (abbreviated "cfDNA") are used interchangeably and refer to DNA molecules freely circulating in the blood. Cell-free DNA molecules are mostly less than 400 bps in length, and even less than 300 bp, or even less than 200 bps, in length.

As used herein, the terms "DNA from white blood cells" "white blood cell DNA" "contaminating white blood cell DNA" and the like refer to DNA released from white blood cells. White blood cell DNA is mostly composed of DNA fragments of more than 10 Kb in length.

As used herein, the phrases "determining plasma separation efficiency", "determining that a plasma sample is separated", "determining that a plasma sample is sufficiently/efficiently separated" and the like are interchangeable and refer to determining that the level of contaminating white blood cell DNA in the plasma is such that it does not interfere with analysis of the cell-free DNA. It is noted that different diagnostic applications involving analysis of cell-free DNA may require different levels of purity of the plasma (i.e., may be characterized by different levels of white blood cell DNA contamination that are tolerated). Thus, a threshold above which a plasma sample is determined to be separated, such as a threshold ΔCq between the short and long amplicons amplified according to the present invention, may be different for different assays. The threshold may be set based on the requirements of a particular diagnostic assay.

Selection of First and Second Genomic Loci and Design of Primers to Produce Short and Long Amplicons:

The assay for evaluating the quality of plasma separation disclosed herein includes a duplex PCR with primers which produce a short amplicon (e.g., ~100 bp) from a first genomic locus and a long amplicon (e.g., ~500 bp) from a second genomic locus. The short and long amplicons produce distinct signal intensity differences for plasma DNA and whole blood DNA, such as distinct ΔCq values for plasma DNA and whole blood DNA.

The DNA in plasma is not simply fragmented genomic DNA, but rather it is a biased representation of the genome, where some genomic loci are under-represented, and other genomic loci are over-represented in relation to whole blood DNA. Pairs of short and long amplicons that produce distinct ΔCq values for plasma and whole blood DNA include pairs of short and long amplicons from genomic loci equally represented in plasma DNA, and pairs of short and long amplicons in which the long amplicon is from a genomic locus under-represented in plasma DNA compared to the genomic locus of the short amplicon.

When such pairs of loci are amplified with primers which have the same efficiency, differences in their amplification levels reflect the proportion of short versus long DNA fragments in the sample, where lower amplification level of the long amplicon reflects lower amounts of long DNA fragments in the sample and accordingly better separation of the plasma.

Thus, in some embodiments, the first and second genomic loci are equally represented in plasma DNA. In additional embodiments, the second genomic locus is under-represented in plasma DNA compared to the first locus. According to some embodiments, the method of the present invention comprises: (a) obtaining DNA from a plasma sample; (b) generating by PCR co-amplification a first amplification product of 70-150 bps from a first genomic locus using a first primer pair and a second amplification product of at least 350 bps from a second genomic locus using a second primer pair, wherein said first and second genomic loci are equally represented in plasma DNA or the second genomic locus is under-represented in plasma DNA compared to the first locus; (c) calculating a signal intensity for each of said first and second amplification products; and d) determining that the plasma sample is separated when the difference between the signal intensities is above a predefined threshold.

In some embodiments, the method of the present invention comprises: (a) obtaining DNA from a plasma sample; (b) generating by real-time PCR amplification a first amplification product of 70-150 bps from a first genomic locus using a first primer pair and a second amplification product of at least 350 bps from a second genomic locus using a second primer pair, wherein said first and second genomic loci are equally represented in plasma DNA or the second genomic locus is under-represented in plasma DNA compared to the first locus; (c) calculating a Cq value for each of said first and second amplification products; and d) determining that the plasma sample is separated when the ΔCq (Cq(second)−Cq(first)) is above a predefined threshold ΔCq.

In some embodiments, there is provided herein a method for analyzing a plasma sample, comprising: (a) obtaining DNA from a plasma sample: (b) generating by real-time PCR amplification a first amplification product of 70-150 bps from a first genomic locus using a first primer pair and a second amplification product of at least 350 bps from a second genomic locus using a second primer pair, wherein said first and second genomic loci are equally represented in plasma DNA or the second genomic locus is under-represented in plasma DNA compared to the first locus: (c) determining a Cq value for each of said first and second amplification products; and optionally (d) calculating ΔCq (Cq(second)−Cq(first)), wherein the first and second amplification products produce distinct ΔCq for plasma DNA and whole blood DNA.

Selecting two genomic loci that are equally represented in cell-free plasma DNA and designing short and long amplicons from these loci can be performed, for example, as follows:

1. Choosing random pairs of genomic loci, Loci with GC content of between 30-60% may be selected, for example;
2. Designing primer pairs for their amplification which produce short (~100 bp) amplicons;

3. Determining the efficiency of the primer pairs in PCR on whole blood DNA in single-plex (separate) reactions.

Methods for determining efficiency of primers are known in the art. For example, efficiency of a primer pair can be performed by (i) selecting a particular concentration of the primers; (ii) conducting real-time PCR reactions on serial dilutions of a template DNA (e.g., whole blood DNA) and determining Ce values for each reaction (each dilution); (ii) generating a standard curve by plotting the Cq values against the log of starting quantity of the template for each dilution; (iv) calculating a slope for the standard curve; and (v) determining reaction efficiency based on the slope. Typically, the efficiency is calculated using the following formula: Efficiency=$10^{-1/slope}$. Amplification efficiency is also frequently presented as a percentage, that is, the percent of template that was amplified in each cycle. To calculate a percentage the following formula is applied: % Efficiency= (Efficiency−1)×100.

4. Eliminating pairs of genomic loci for which the efficiency of the primers is not equal, and continuing with pairs of genomic loci for which the efficiency of the primers is equal;

5. For each pair of genomic loci, comparing the copy number of the loci in plasma DNA and eliminating the pairs with different copy numbers (in other words, eliminating the pairs with a representation bias in plasma DNA, in which one of the loci is over represented in plasma DNA compared to the other, and selecting the pairs with equal representation in plasma DNA).

Evaluating differences in copy number in plasma DNA may be performed, for example, by: (i) quantitatively amplifying the genomic loci from plasma DNA and from whole blood DNA using the primers selected in the previous steps which amplify short amplicons from each locus with equal efficiency; (ii) For each DNA sample (plasma DNA or whole blood DNA), calculating a ΔCq between the two loci; and (iii) determining the difference in copy number according to the ΔCq in plasma DNA vs. the ΔCq in whole blood DNA.

6. For a selected pair of genomic loci that was found to be equally represented in plasma DNA in the previous step, designing primers for a long (>350 bp) amplicon for one of the genomic loci in the pair;

7. Determining the efficiency of the primers of the long amplicon on whole blood DNA as described above;

8. Calibrating the efficiencies of the primers of the short amplicon and the primers of the long amplicon until the same efficiency is achieved. The efficiency can be modified by slightly changing the sequences of the primers, for example by adding/deleting bases from the 5' or 3' ends of the primers. Alternatively or additionally, primer concentration can be adjusted in order to achieve equal efficiency.

The resulting primers amplify with the same efficiency (although with differently-sized amplicons) two genomic loci that are represented equally in plasma DNA.

Designing pairs of short and long amplicons in which the long amplicon is from a genomic locus under-represented in plasma DNA compared to the genomic locus of the short amplicon can be performed, for example, as follows:

1. Choosing random pairs of genomic loci;
2. Designing primers for their amplification which produce short (~100 bp) amplicons;
3. Determining the efficiency of the primers in PCR on whole blood DNA in single-plex (separate) reactions, as described above.
4. Eliminating the pairs of genomic loci for which the efficiency of the primers is not equal, and continuing with the pairs of genomic loci for which the efficiency of the primers is equal;
5. For each pair of genomic loci, comparing the copy number of the loci in plasma DNA (as described above), and selecting pairs with different copy numbers, in which one of the loci is under-represented in plasma DNA compared to the other;
6. For a selected pair of loci, designing primers for a long (>350 bp) amplicon for the genomic locus that was found to be under-represented compared to the other;
7. Determining the efficiency of the primers of the long amplicon on whole blood DNA, as described above;
8. Calibrating the efficiencies of the primers of the short amplicon and the primers of the long amplicon until the same efficiency is achieved. The efficiency can be modified by slightly changing the sequences of the primers, for example by adding/deleting bases from the 5' or 3' ends of the primers. Alternatively or additionally, primer concentration can be adjusted in order to achieve equal efficiency.

As detailed above, efficiency of primers/PCR reactions can be measured by known methods (for example by generating a standard curve and calculating the efficiency based on the slope of the standard curve), and expressed as a numerical value or as a percentage.

As used herein, the term "equal efficiency" with respect to amplification efficiency/primer efficiency refers to the exact same efficiency (e.g., the same percentage efficiency) and also to differences of up to 5% in efficiency. "Primers of equal efficiency" encompasses adjustment of primer sequence and/or concentration in the reaction in order to achieve equal efficiency. Primers with equal efficiency advantageously avoid bias of the results due to primer efficiency.

As used herein, the term "equally represented in plasma DNA" with respect to genomic loci refers to genomic loci that have the same copy number in plasma DNA. The term encompasses the exact same representation (i.e., the exact copy number) and also differences of up to 5% in representation. The term "under-represented in plasma DNA", referring to a certain locus compared to another locus, indicates that this certain locus has a lower copy number in plasma DNA compared to the other locus. The term indicates a difference of more than 5% in representation.

Copy number can be measured by known methods, for example, as detailed above.

When designing the short and long amplification products for use with the methods of the present invention, the CG content of the amplified sequence may be taken into account. For example, in some embodiments, the CG content of each amplification product is lower than 50%.

Plasma Sample Processing

As used herein, the terms "whole blood" and "blood" refer to a blood sample that has not been fractionated and contains both cellular components (red blood cells, white blood cells, and platelets) and fluid components.

The term "plasma" refers to the liquid remaining after a whole blood sample is subjected to a separation process to remove the blood cells.

According to some embodiments, plasma samples to be analyzed using the methods of the present invention are derived from human subjects. According to some embodiments, the plasma samples originate from subjects with a malignant disease such as a particular type of cancer, or subjects suspected of having a malignant disease such as one or more types of cancer. According to additional embodiments, the plasma samples originate from healthy subjects. The term 'healthy subjects' as used herein refers to subjects not diagnosed with a malignant disease such as a certain type of cancer and/or subjects not suspected of having cancer, and/or subjects not susceptible to having cancer.

The plasma samples may be samples separated from whole blood using any method of separation. An exemplary procedure is described in the Examples section below. The plasma sample may be a freshly isolated sample or a sample that was stored for a certain period of time before the analysis.

The terms "DNA from", "DNA obtained from" and the like refer to DNA isolated from a plasma sample (for example extracted from the plasma using methods known in the art), as well as to a plasma sample as is, namely, a plasma sample containing DNA.

In some embodiments, the methods of the present invention comprise providing a plasma sample. In some embodiments, the methods of the present invention comprise providing DNA from a plasma sample.

Generation of Amplification Products

The methods disclosed herein comprise according to some embodiments co-amplifying a 70-150 bps amplicon from a first genomic locus using a first primer pair, and a 350-650 bps amplicon from a second genomic locus using a second primer pair.

The first and second amplification products of the present invention are generated by amplification using pairs of reverse and forward primers designed as known in the art to specifically generate each amplification product.

The length of the first (short) amplification product is typically between 70-150 bps, for example between 80-150 bps, 100-150 bps, 100-130 bps. Each possibility represents a separate embodiment of the present invention.

The length of the second (long) amplification products is at least 350 bps, typically between 350-750 bps, between 350-650 bps, between 350-600 bps, 350-550 bps or 400-500 bps. Each possibility represents a separate embodiment of the present invention.

In some embodiments, the first amplification product comprises a sequence as set forth in SEQ ID NO: 1. In some embodiments, the first amplification product consists of the sequence set forth in SEQ ID NO: 1. In some embodiments, the first amplification product comprises a sequence as set forth in SEQ ID NO: 10. In some embodiments, the first amplification product consists of the sequence set forth in SEQ ID NO: 10.

In some embodiments, the second amplification product comprises a sequence as set forth in SEQ ID NO: 2. In some embodiments, the second amplification product consists of the sequence set forth in SEQ ID NO: 2. In some embodiments, the second amplification product comprises a sequence as set forth in SEQ ID NO: 7. In some embodiments, the second amplification product consists of the sequence set forth in SEQ ID NO: 7. In some embodiments, the second amplification product comprises a sequence as set forth in SEQ ID NO: 8. In some embodiments, the second amplification product consists of the sequence set forth in SEQ ID NO: 8. In some embodiments, the second amplification product comprises a sequence as set forth in SEQ ID NO: 9. In some embodiments, the second amplification product consists of the sequence set forth in SEQ ID NO: 9.

In some embodiments, the first and second amplification products comprise sequences as set forth in SEQ ID NO: 1 and SEQ ID NO: 2, respectively. In additional embodiments, the first and second amplification products consist of sequences as set forth in SEQ ID NO: 1 and SEQ ID NO: 2, respectively.

In some embodiments, the primer pair for amplifying the first amplification product is: SEQ ID NO: 3 (forward) and SEQ ID NO: 4 (reverse).

In some embodiments, the primer pair for amplifying the second amplification product is: SEQ ID NO: 5 (forward) and SEQ ID NO: 6 (reverse).

In plasma samples contaminated with high levels of white blood cell DNA, both short and long DNA fragments are found in the sample, resulting in efficient amplification of both the short and long amplification products. In plasma samples well separated from the cellular fraction of the blood, there are mainly (or only) short cell-free DNA fragments.

In some samples, the short amplification product is amplified with greater efficiency compared to the long amplification product. The better the separation of the plasma sample the better the amplification of the short amplification product compared to the long amplification product, reflected, for example, in increasing delta Cq values between the Cq of the long amplicon and the Cq of the short amplicon (Cq (long)− Cq (short)) following quantitative real-time PCR.

The terms "genomic locus" or "locus" as used herein are interchangeable and refer to a DNA sequence at a specific position on a chromosome. The specific position may be identified by the molecular location, namely, by the numbers of the starting and ending base pairs on the chromosome. A variant of a DNA sequence at a given genomic position is called an allele. Alleles of a locus are located at identical sites on homologous chromosomes. Loci include gene sequences as well as other genetic elements (e.g., intergenic sequences).

As used herein, "amplification" refers to an increase in the number of copies of one or more nucleic acid sequence of interest. Amplification is typically performed by polymerase chain reaction (PCR) in the presence of a PCR reaction mixture which may include a suitable buffer supplemented with a DNA template, a polymerase (usually Taq Polymerase), dNTPs, primers and probes (as appropriate), as known in the art.

The term "polynucleotide" as used herein include polymeric forms of nucleotides of any length, either deoxyribonucleotides or ribonucleotides, or analogs thereof. The term "oligonucleotide" is also used herein to include a polymeric form of nucleotides, typically of up to 100 bases in length.

The terms "amplification product" and "amplicon" are used interchangeably and collectively refer to nucleic acid molecules of a particular target sequence that are generated and accumulated in an amplification reaction. The terms generally refer to nucleic acid molecules generated by PCR using a given set of amplification primers.

As used herein, a "primer" defines an oligonucleotide which is capable of annealing to (hybridizing with) a target sequence, thereby creating a double stranded region which can serve as an initiation point for DNA synthesis under suitable conditions. The terminology "primer pair" refers herein to a pair of oligonucleotides which are selected to be used together in amplifying a selected nucleic acid sequence by one of a number of types of amplification processes, preferably PCR. As commonly known in the art, the primers may be designed to bind to a complementary sequence under selected conditions.

The primers may be of any suitable length, depending on the particular assay format and the particular needs. In some embodiments, the primers may include at least 15 nucleotides in length, preferably between 19-2.5 nucleotides in length. The primers may be adapted to be especially suited to a chosen nucleic acid amplification system. As commonly known in the art, the oligonucleotide primers may be designed by taking into consideration the melting point of hybridization thereof with their targeted sequence.

The methods disclosed herein involve simultaneous amplification of more than one target sequence (first and second amplification products) in the same reaction mixture, a process known as multiplex amplification or co-amplification. This process requires simultaneous use of two primer pairs. As known in the art, the primers may be designed such that they can work at the same annealing temperature during amplification. In some embodiments, primers with similar melting temperature (Tm) are used in the method disclosed herein. A Tm variation of between about 3°-5° C. is considered acceptable for primers used in a pool.

According to some embodiments, amplification of the genomic loci is carried out using real-time PCR (RT-PCR), also known as quantitative PCR (qPCR), in which simultaneous amplification and detection of the amplification products are performed.

In some embodiments, detection of the amplification products in RT-PCR may be achieved using polynucleotide probes, typically fluorescently-labeled polynucleotide probes.

As used herein, "polynucleotide probes" or "oligonucleotide probes" are interchangeable and refer to labeled polynucleotides which are complementary to specific sub-sequences within the nucleic acid sequences of loci of interest, for example, within the sequences of first (short) and second (long) genomic loci as described herein. In some embodiments, detection is achieved by using TaqMan assays based on combined reporter and quencher molecules (Roche Molecular Systems Inc.). In such assays, the polynucleotide probes have a fluorescent moiety (fluorophore) attached to their 5' end and a quencher attached to the 3' end. During PCR amplification, the polynucleotide probes selectively hybridize to their target sequences on the template, and as the polymnerase replicates the template it also cleaves the polynucleotide probes due to the polymerase's 5'-nuclease activity. When the polynucleotide probes are intact, the close proximity between the quencher and the fluorescent moiety normally results in a low level of background fluorescence. When the polynucleotide probes are cleaved, the quencher is decoupled from the fluorescent moiety, resulting in an increase of intensity of fluorescence. The fluorescent signal correlates with the amount of amplification products, i.e., the signal increases as the amplification products accumulate.

As used herein, "selectively hybridize to" (as well as "selective hybridization," "specifically hybridize to," and "specific hybridization") refers to the binding, duplexing, or hybridizing of a nucleic acid molecule (such as a primer or a probe) preferentially to a particular complementary nucleotide sequence under stringent conditions. The term "stringent conditions" refers to conditions under which a nucleic acid molecule will hybridize preferentially to its target sequence and to a lesser extent to, or not at all to, other non-target sequences. A "stringent hybridization" in the context of nucleic acid hybridization is sequence-dependent, and differs under different conditions, as known in the art.

Polynucleotide probes may vary in length. In some embodiments, the polynucleotide probes may include between 15-30 bases. In additional embodiments, the polynucleotide probes may include between 25-30 bases. In some embodiments, the polynucleotide probes may include between 20-30 bases, for example, 20 bases, 21 bases, 22 bases, 23 bases, 24 bases, 25 bases, 26 bases, 27 bases, 28 bases, 29 bases, 30 bases. Each possibility represents a separate embodiment of the present invention.

Polynucleotide probes may be designed to bind to either stand of the template. Additional considerations include the Tm of the polynucleotide probes, which should preferably be compatible to that of the primers. Computer software may be used for designing the primers and probes.

As noted above, the methods disclosed herein involve simultaneous amplification of more than one target sequence in the same reaction mixture. In order to distinguish between multiple target sequences that are amplified in parallel, polynucleotide probes labeled with distinct fluorescent colors may be used.

In some embodiments, the polynucleotide probes form a fluorophore/quencher pairs as known in the art and include, for example, FAM-TAMRA, FAM-BHQ1, Yakima Yellow-BHQ1, ATTO550-BHQ2 and ROX-IBHQ2.

In some embodiments, the dye combinations may be compatible to the RT-PCR thermocycler of choice.

In some embodiments, fluorescence may be monitored during each PCR cycle, providing an amplification plot showing the change of fluorescent signals from the probes as a function of cycle number.

In the context of RT-PCR, the following terminology is used:

"Quantification cycle" ("Cq") refers to the cycle number in which fluorescence increases above a threshold fluorescence, set automatically by software or manually by the user. In some embodiments, the threshold fluorescence may be constant for all amplicons and may be set in advance, prior to carrying out the amplification and detection. In other embodiments, the threshold fluorescence may be defined separately for each amplicon after the run, based on the maximum fluorescence level detected for this amplicon during the amplification cycles. In some embodiments, the threshold fluorescence may be a value above baseline fluorescence, and/or above background noise, and within the exponential growth phase of the amplification plot. "Baseline" refers to the initial cycles of PCR where there is little to no change in fluorescence.

Computer software may be used to analyze amplification plots and determine baseline, threshold and Cq.

In plasma samples well separated from the cellular components, with no cellular DNA or with residual amounts of cellular DNA, there is essentially no template DNA for amplification of the long amplicon. Following PCR using the first and second primer pairs, the short amplicon is amplified with high efficiency, while a very low amount of amplification product is formed for the long amplicon, if any. The amplification plot would show a low Cq value for the short amplicon (amplification product is detected following a relatively low number of amplification cycles) and a high Cq value for the long amplicon (amplification product is detected following a relatively high number of amplification cycles).

In plasma samples contaminated with cellular genomic DNA, the higher the contamination the lower the Cq value of the long amplicon.

The difference between the Co of the short amplicon and the Cq of the long amplicon is indicative of the quality of separation of the plasma sample.

Determining Efficiency of Separation

The efficiency of plasma separation is determined based on differences in signal intensities, such as differences in Cq values, between the short and long amplification products following real-time PCR.

The term "signal intensity" as used herein refers to a measure reflecting the amount of a sequence-specific amplification product, corresponding to the initial amount of copies of the target sequence. However, the signal intensity may not indicate actual amounts of amplification products/target sequences, and may not involve calculation of any absolute amounts of amplification products/target sequences. Thus, in some embodiments, for calculating signal intensities of amplification products, no standard curve or reference DNA are employed, since it is unnecessary to calculate actual DNA amounts per se.

In some embodiments, amplification and detection of amplification products are carried out by RT-PCR where the signal intensity of a specific amplification product is represented by the Cq calculated for this amplification product.

In some embodiments, in case of no amplification or very little amplification the Cq is determined as "infinity". In some embodiments, in such cases the numerical value of the delta Cq is set to be 14.

In some embodiments, calculating a difference between signal intensities of the first and second amplification products in the DNA sample comprises determining the Cq for each locus, and calculating the difference between the Cq values ($\Delta$Cq). In some embodiments, calculating a difference between signal intensities of the two amplification products is carried out by calculating Cq(long)–Cq(short).

For example, assuming a first (short) Cq of a first amplification product being "25" and a second Cq of a second (long) amplification product being "30", the Cq(long)–(Cq(short) is "5".

In some embodiments, computer software is used for calculating a difference between Cqs of amplification products.

In some embodiments, a calculated delta Cq indicates that a tested plasma sample is sufficiently separated from whole blood when the calculated delta Cq is above a predefined threshold delta Cq.

A "threshold delta Cq" refers to a delta Cq that differentiates between sufficiently separated plasma samples to poorly or not separated plasma samples. The threshold is typically set to reflect contaminating white blood cell DNA below a certain amount or percentage, which does not interfere with analysis of cell-free DNA, As noted above, different diagnostic applications involving analysis of cell-free DNA may require different levels of purity of the plasma (i.e. may be characterized by different levels of white blood cell DNA contamination that are tolerated). For example, in some embodiments, a separated plasma sample is a plasma sample containing less than 50% contaminating white blood cell DNA, less than 40% contaminating white blood cell DNA, less than 30% contaminating white blood cell DNA, less than 20% contaminating white blood cell DNA, less than 10% contaminating white blood cell DNA, less than 5% contaminating white blood cell DNA, less than 1% contaminating white blood cell DNA. Each possibility represents a separate embodiment of the present invention.

A threshold $\Delta$Cq above which a plasma sample is determined to be separated may be set based on the requirements of a particular diagnostic assay.

For example, in some embodiments, the threshold $\Delta$Cq is 1 cycle, reflecting 50:50 ratio between contaminating white blood cell DNA and cell-free DNA in the sample.

In some embodiments, the threshold $\Delta$Cq is about 1 cycle. In some embodiments, the threshold $\Delta$Cq is at least 1 cycle. In additional embodiments, the threshold $\Delta$Cq is at least 2 cycles. In yet additional embodiments, the threshold $\Delta$Cq is at least 3 cycles. In yet additional embodiments, the threshold $\Delta$Cq is at least 4 cycles.

In some embodiments, determining the threshold $\Delta$Cq includes: (i) spiking a plasma sample with different amounts (or percentage) of buffy coat or whole blood DNA to obtain a series of plasma samples with different degrees of white blood cell DNA contamination; (ii) performing real-time PCR for a pair of short and long amplicons in each sample and determining the Cq for each amplicon in each sample; (iii) calculating $\Delta$Cq for each sample (for each degree of white blood cell DNA contamination) and determining the threshold according to the maximal contamination that a particular assay/application permits.

In some embodiments, the methods of the present invention comprise providing a threshold delta Cr.

In some embodiments, the threshold values are statistically significant values. Statistical significance is often determined by comparing two or more populations, and determining a confidence interval (CI) and/or a p value. In some embodiments, the statistically significant values refer to confidence intervals (CI) of about 90%, 95%, 97.5%, 98%, 99%, 99.5%, 99.9% and 99.99%, while preferred p values are less than about 0.1, 0.05, 0.025, 0.02, 0.01, 0.005, 0.001 or less than 0.0001. Each possibility represents a separate embodiment of the present invention. According to some embodiments, the p value of the threshold value is at most 0.05.

As used herein, the term "about", when referring to a measurable value is meant to encompass variations of +/−10%, more preferably +/−5%, even more preferably +/−1%, and still more preferably +/−0.1% from the specified value.

Kits and Systems

In some embodiments, there is provided herein a kit for determining the efficiency of plasma separation from whole blood, according to the methods of the present invention.

In additional embodiments, there is provided herein a system for determining the efficiency of plasma separation from whole blood, according to the methods of the present invention.

In some embodiments, the kit comprises a pair of primers for amplification of a first amplification product of 70-150 bps from a first genomic locus and a second amplification product of at least 350 bps from a second genomic locus: means for detecting the first and second amplification products; and instruction manual for carrying out the determination of plasma separation efficiency according to the method disclosed herein. In some embodiments, the instruction manual may be an electronic instruction manual.

In some embodiments, the instruction manual may provide a threshold delta Cq, above which a plasma sample is determined to be separated.

In some embodiments, the instruction manual may include instructions for performing the method steps described herein.

In some embodiments, the instruction manual may include instructions directing the correlation between delta Cq and separation.

In some embodiments, the instruction manual may include instructions for carrying out the determination of plasma separation using a computer software stored on a computer-readable medium, the computer software directs a computer processor to determine plasma separation based on the difference in signal intensities of the first and second amplification products.

In some embodiments, the kit may further comprise a computer readable medium storing a computer software that directs a computer processor to determine plasma separation based on the difference in signal intensities of the first and second amplification products.

In some embodiments, a system of the present invention comprises: (i) a first primer pair, for generating by PCR a first amplification product of 70-150 bps from a first genomic locus; (ii) a second primer pair, for generating by PCR a second amplification product of at least 350 bps, from a second genomic locus; (iii) probes for detecting the first and second amplification products, to determine a signal intensity for each amplification product; and (iv) computer software stored on a computer readable medium that directs a computer processor to determine plasma separation based on the difference in signal intensities of the first and second amplification products.

In some embodiments, the computer software of the present invention directs the computer processor to perform the following steps: determining a signal intensity for each of the first and second amplification products; and calculating a difference between the signal intensities. In some embodiments, the computer software further directs the computer processor to compare the calculated difference to a predefined threshold, and, based on the comparison, to output whether the plasma sample is separated. In some embodiments, the computer software may be a computer software that directs a computer processor to calculate at least one of Cq and delta Cq.

In some embodiments, the computer software receives as an input parameters or raw data of a real-time PCR run. In some embodiments, the computer software directs a computer processor to analyze the real-time PCR run to determine signal intensities (Cqs) and signal intensity differences (ΔCq).

The computer software includes processor-executable instructions that are stored on a non-transitory computer readable medium. The computer software may also include stored data. The computer readable medium is a tangible computer readable medium, such as a compact disc (CD), magnetic storage, optical storage, random access memory (RAM), read only memory (ROM), or any other tangible medium.

In some embodiments, the system comprises a processor, configured to carry out the following: determining plasma separation based on comparison of a calculated signal intensity difference between the first and second amplification product to a threshold signal intensity difference.

In some embodiments, the system comprises machinery for carrying out the generation of amplification products, such as a real-ti me PCR machine.

In some embodiments, the kit or system comprises fluorescently-labeled oligonucleotide probes complementary to sub-sequences within the first and second amplification products, for detecting the first and second amplification products.

In some embodiments, the kit or system comprises first and second primer pairs, each designed to selectively amplify a fragment of the genome to generate first and second amplification products, as described herein.

In some embodiments, the first primer pair is: SEQ ID NO: 3 (forward) and SEQ ID NO: 4 (reverse).

In some embodiments, the second primer pair is: SEQ ID NO: 5 (forward) and SEQ ID NO: 6 (reverse).

In some embodiments, the kit or system may further include at least one additional ingredient needed for amplification and detection of amplification products, such as DNA polymerase and nucleotide mix.

In some embodiments, the kit or system may further include suitable reaction buffers and a written protocol for performing the assay. The written protocol may comprise instructions for performing any of the steps disclosed herein, including but not limited to, PCR cycling parameters, Cq determination and analysis, and a delta Cq threshold.

It is understood that the computer-related methods, steps, processes described herein are implemented using software stored on non-volatile or non-transitory computer readable instructions that when executed configure or direct a computer processor or computer to perform the instructions.

The following examples are presented in order to more fully illustrate certain embodiments of the invention. They should in no way, however, be construed as limiting the broad scope of the invention. One skilled in the art can readily devise many variations and modifications of the principles disclosed herein without departing from the scope of the Invention.

EXAMPLES

Example 1—Testing Plasma Samples

The following pair of short and long amplicons was designed for testing DNA from plasma samples, plasma samples contaminated with leukocytes and whole blood samples:

```
"Short" (126 bps)(SEQ ID NO: 1):
GTCTTTGTGACATTGAGTTACAGGGCTTTGACTCCTGGGTCTAAAAATTA

CACCAAATATTGTTAAATCTTAAACACTAACAGCAATTCAAGCCTCATCT

TCAGGTCCTGGAGAAGATGCCAATAT
```

The short amplicon corresponds to position 155565467-155565601 on chromosome 1 (according to hg18). The short amplicon was designed for amplification using the following primers:

```
Forward (SEQ ID NO: 3):
GTCTTTGTGACATTGAGTTACAG

Reverse (SEQ ID NO: 4):
ATATTGGCATCTTCTCCAGGAC

"Long" (450 bps)(SEQ ID NO: 2):
GTCAGCCTTTATTATCACTTTGCAATACAAAGAAAGCAAGGTGAAGACTA
ACTTTTCTCTTGTACAGAATCATCAGGCTAAATTTTTGGCATTATTTCAG
TCCTTGGAGACATCTGAGAGATTCCGGGATGCCAGTGGTGCCTCTCTGGC
CACACTGACAACAAATAATTCACCTAAGGAATAGTTCACTTCAGCTATTT
TTTGCTACTCATTGGTTGTCAGTGCCATTGAGGAGAGCTCAGTGTAGATC
AAAGAAAACGGTGTAGATCAAAGAAAACGGTGATTCGGTGATTGTTCCCC
TTCTTCCCAGCCACCCACCATCTGAACCTAATGCATCATTGTACAATGGC
CGTAAAGGATGACAAGGGACTCAGCAATCAGTTCCTGGAGGAAATGATGC
TGTGGCTTTTGGCTGGTGGCACCATCATCCTCAGTCATCAGTCAGAGTCA
```

The long amplicon corresponds to position 121380810-121381259 on chromosome 7 (according to hg18). The long amplicon was designed for amplification using the following primers:

```
Forward (SEQ ID NO: 5): GTCAGCCTTTATTATCACTTTGC

Reverse (SEQ ID NO: 6): TGACTCTGACTGATGACTGAGG
```

Blood samples were collected from human subjects and processed to obtain plasma or plasma+buffy coat (leukocytes and platelets), or kept unprocessed (whole blood).

To obtain plasma+buffy coat, the blood tube (containing anticoagulant) was centrifuged at 1500 g for 10 min to separate the blood components. After centrifugation the plasma layer was collected with the buffy coat layer (leukocytes and platelets) and transferred to a new tube.

To obtain plasma samples, the blood tube (containing anticoagulant) was centrifuged at 1500 g for 10 min to separate the blood components. After centrifugation the plasma layer was collected (without getting close to the buffy coat) and transferred to a new tube. The plasma was centrifuged again (1500 g for 10 min) and the pure plasma was transferred to a new tube.

DNA was extracted from the samples using QIAamp® Circulating Nucleic Acid Kit. The extracted DNA was subjected to real time (RT)-PCR to amplify the above short and long amplicons from each sample (co-amplification).

The amplification reaction (total volume 25 microliter) contained 2 microliters of the extracted DNA (DNA concentration was not measured before amplification), 0.0-0.5 M primers, dNTPs and a reaction buffer. To enable detection of amplification products during amplification, fluorescently-labeled polynucleotide probes for each amplicon were added to the reaction (FAM and JOE labels, for the long and short amplicons, respectively). The primers and probe conciliation of each amplicon were adjusted in order to achieve equal efficiency. RT-PCR reactions were carried out in an ABI 7500 FastDx instrument with the following PCR program: 95° C., 10 min→45×(95° C., 15 sec)→60° C., 1 min.

Following amplification, quantitative PCR plots showing the change of fluorescent signals from the probes as a function of cycle number were analyzed to calculate the quantification cycle (Cq) for each amplicon. A ΔCq was calculated between the Cq of the long amplicon and the Cq of the short amplicon (Cq (long)–Cq (short)).

Figure 1B:
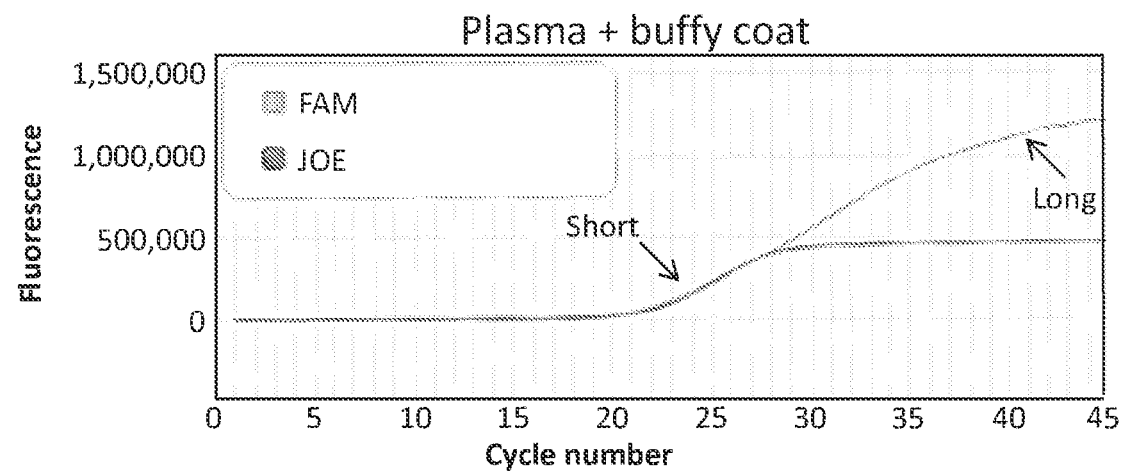
Figure 1C:
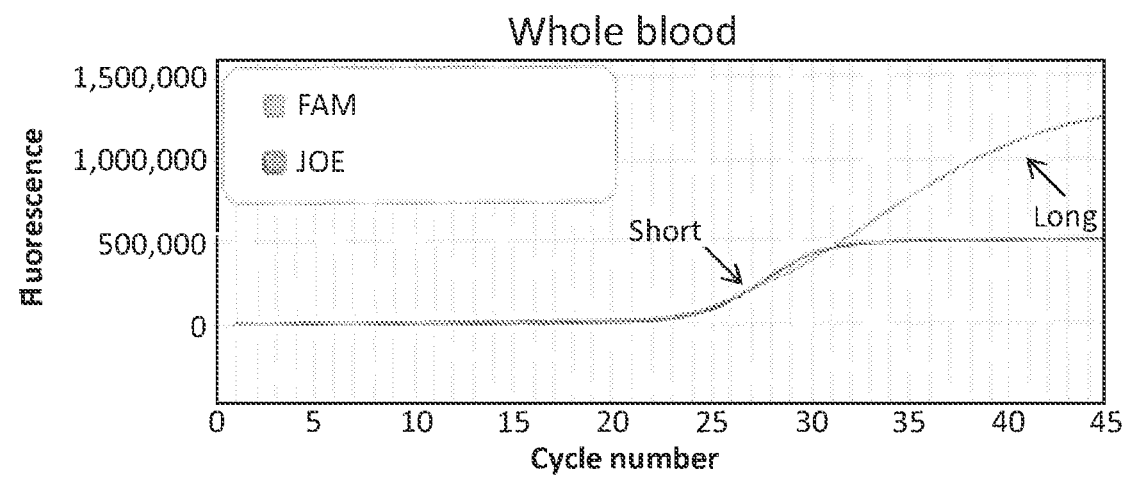

FIGS. 1A-C show exemplary quantitative PCR plots of the short and long amplification products in DNA samples from plasma (FIG. 1A, ΔCq=3), plasma contaminated with leukocytes (FIG. 1B, ΔCq=(–0.4)) and DNA from whole blood (FIG. 1C, ΔCq=(–0.2)).

In the plasma samples, in which the amount of DNA from white blood cells is very low, the long amplicon was amplified with low efficiency. It rose roughly 3-4 cycles later than the short amplicon.

In the samples of plasma contaminated with leukocytes and in the whole blood samples, in which white blood cell DNA levels are high, the long and short amplicons were amplified with similar efficiency. The long amplicon rose roughly on the same cycle as the short amplicon.

The foregoing description of the specific embodiments will so fully reveal the general nature of the invention that others can, by applying current knowledge, readily modify and/or adapt for various applications such specific embodiments without undue experimentation and without departing from the generic concept, and therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed chemical structures and functions may take a variety of alternative forms without departing from the invention.

The invention claimed is:

1. A method for determining the efficiency of plasma separation from whole blood, the method comprising:
   (a) separating plasma from a whole blood sample to provide a plasma sample;
   (b) obtaining DNA from a plasma sample;
   (c) generating by PCR co-amplification:
      (i) a first amplification product of 70-150 bps from a first genomic locus using a first primer pair, wherein the first amplification product comprises the sequence set forth in SEQ ID NO: 1 or SEQ ID NO: 10, and
      (ii) a second amplification product of at least 350 bps from a second genomic locus using a second primer pair, wherein the second amplification product comprises the sequence set forth in SEQ ID NO: 2, SEQ ID NO: 7, SEQ ID NO: 8, or SEQ ID NO: 9;
   (d) calculating a signal intensity for each of said first and second amplification products, wherein said first and second amplification products produce distinct signal intensity differences for plasma DNA and whole blood DNA; and
   (e) determining that the plasma sample is separated with acceptable efficiencies when the difference between the signal intensities is above a predefined threshold.

2. The method of claim 1, wherein step (c) is performed using real-time PCR.

3. The method of claim 2, wherein the method further comprises adding fluorescent probes for specifically detecting the first and second amplification products.

4. The method of claim 3, wherein the signal intensity is quantification cycle (Cq), and wherein the plasma sample is determined to be separated based on the difference between the Cq values (ΔCq) of the first and second amplification products.

5. The method of claim 4, wherein the plasma sample is determined to be separated when the ΔCq (Cq (second)-Cq (first)) is above a predefined threshold ΔCq.

6. The method of claim 1, wherein the first amplification product is of 100-150 bps.

7. The method of claim 1, wherein the second amplification product is of 350-700 bps.

8. The method of claim 1, wherein the second amplification product is of 350-550 bps.

9. The method of claim 1, wherein the first amplification product consists of the sequence set forth in SEQ ID NO: 1 or SEQ ID NO: 10.

10. The method of claim 1, wherein the second amplification product consists of the sequence set forth in SEQ ID NO: 2, SEQ ID NO: 7, SEQ ID NO: 8 or SEQ ID NO: 9.

11. The method of claim 1, wherein the first and second amplification products comprise sequences as set forth in SEQ ID NO: 1 and SEQ ID NO: 2, respectively.

12. The method of claim 1, wherein the first and second amplification products consist of sequences as set forth in SEQ ID NO: 1 and SEQ ID NO: 2, respectively.

13. The method of claim 1, wherein the plasma sample is derived from a human blood sample.

14. The method of claim 11, wherein the first primer pair is SEQ ID NO: 3 (forward) and SEQ ID NO: 4 (reverse), and the second primer pair is SEQ ID NO: 5 (forward) and SEQ ID NO: 6 (reverse).

* * * * *